(12) United States Patent
Jo et al.

(10) Patent No.: US 10,918,156 B2
(45) Date of Patent: Feb. 16, 2021

(54) PRESSURE DETECTION SENSOR AND PRESSURE DETECTION INSOLE INCLUDING SAME

(71) Applicant: LG INNOTEK CO., LTD., Seoul (KR)

(72) Inventors: Hyun Jin Jo, Seoul (KR); Won Keun Cho, Seoul (KR); Jeong Han Kim, Seoul (KR); Soo Min Lee, Seoul (KR); Ji Na Lee, Seoul (KR); In Hee Cho, Seoul (KR); Sang A Ju, Seoul (KR)

(73) Assignee: LG INNOTEK CO., LTD., Seoul (KR)

( * ) Notice: Subject to any disclaimer, the term of this patent is extended or adjusted under 35 U.S.C. 154(b) by 158 days.

(21) Appl. No.: 16/302,589

(22) PCT Filed: May 23, 2017

(86) PCT No.: PCT/KR2017/005302
§ 371 (c)(1),
(2) Date: Nov. 16, 2018

(87) PCT Pub. No.: WO2017/204514
PCT Pub. Date: Nov. 30, 2017

(65) Prior Publication Data
US 2019/0289951 A1    Sep. 26, 2019

(30) Foreign Application Priority Data

May 23, 2016   (KR) .................. 10-2016-0062896
Jul. 14, 2016    (KR) .................. 10-2016-0089287

(51) Int. Cl.
*G01L 1/20*   (2006.01)
*A43B 3/00*   (2006.01)
(Continued)

(52) U.S. Cl.
CPC ............ *A43B 3/0005* (2013.01); *A43B 17/00* (2013.01); *A43B 17/006* (2013.01); *A61B 5/00* (2013.01);
(Continued)

(58) Field of Classification Search
USPC .......................................................... 73/172
See application file for complete search history.

(56) References Cited

U.S. PATENT DOCUMENTS 5,408,873 A * 4/1995 Schmidt ............... A43B 3/0005
                                                              600/592
2003/0097878 A1  5/2003 Farringdon et al.
(Continued)

FOREIGN PATENT DOCUMENTS

KR   10-2004-0061001    7/2004
KR   10-2010-0013465    2/2010
(Continued)

OTHER PUBLICATIONS

International Search Report (with English Translation) and Written Opinion dated Aug. 11, 2017 issued in Application No. PCT/KR2017/005302.

*Primary Examiner* — Andre J Allen
(74) *Attorney, Agent, or Firm* — KED & Associates LLP

(57) ABSTRACT

Disclosed in an embodiment is a pressure detection sensor comprising: an elastic layer including a hole; and an electrode layer including a plurality of electrodes arranged on the elastic layer so as to be spaced apart, wherein the elastic layer includes a variable member arranged in the hole, the plurality of electrodes are electrically connected to each other by outside pressure, and at least one of the plurality of electrodes covers a part of the hole.

20 Claims, 9 Drawing Sheets

(51) Int. Cl.

| | |
|---|---|
| *A43B 17/00* | (2006.01) |
| *B32B 3/26* | (2006.01) |
| *B32B 7/12* | (2006.01) |
| *G01L 9/06* | (2006.01) |
| *A61B 5/103* | (2006.01) |
| *A61B 5/00* | (2006.01) |
| *H01B 1/12* | (2006.01) |
| *H01B 1/02* | (2006.01) |

(52) U.S. Cl.
CPC .............. *A61B 5/103* (2013.01); *B32B 3/266* (2013.01); *B32B 7/12* (2013.01); *G01L 1/20* (2013.01); *G01L 9/06* (2013.01); *H01B 1/12* (2013.01); *B32B 2262/103* (2013.01); *B32B 2307/202* (2013.01); *B32B 2437/02* (2013.01); *H01B 1/02* (2013.01)

(56) References Cited

U.S. PATENT DOCUMENTS

| | | | | |
|---|---|---|---|---|
| 2010/0063778 | A1 | 3/2010 | Schrock et al. | |
| 2012/0291563 | A1* | 11/2012 | Schrock | A43B 13/38 73/862.041 |
| 2012/0291564 | A1* | 11/2012 | Amos | A43B 3/0005 73/862.045 |
| 2013/0213145 | A1* | 8/2013 | Owings | A43B 3/0005 73/862.046 |
| 2013/0213146 | A1* | 8/2013 | Amos | G01L 1/20 73/862.046 |
| 2013/0213147 | A1* | 8/2013 | Rice | A43B 7/088 73/862.046 |
| 2014/0130593 | A1* | 5/2014 | Ciou | A61B 5/1038 73/172 |
| 2014/0260677 | A1* | 9/2014 | Dojan | A43B 13/14 73/862.045 |
| 2014/0278125 | A1* | 9/2014 | Balakrishnan | G16H 20/30 702/19 |
| 2017/0265582 | A1* | 9/2017 | Walker | A43B 3/0031 |
| 2019/0000177 | A1* | 1/2019 | Dervish | A43B 7/144 |
| 2019/0003906 | A1* | 1/2019 | Dervish | A61B 5/1038 |
| 2019/0003907 | A1* | 1/2019 | Dervish | A61B 5/6807 |
| 2019/0142097 | A1* | 5/2019 | Moor | A42B 3/046 600/587 |
| 2019/0208865 | A1* | 7/2019 | Walker | G01L 1/12 |
| 2019/0339143 | A1* | 11/2019 | Jarvinen | G01L 1/146 |
| 2020/0092991 | A1* | 3/2020 | Viberg | H01L 23/02 |
| 2020/0182714 | A1* | 6/2020 | Steier | A61B 5/6807 |

FOREIGN PATENT DOCUMENTS

| | | |
|---|---|---|
| KR | 10-2011-0124964 | 11/2011 |
| KR | 10 2014-0004206 | 1/2014 |
| KR | 10-1452748 | 10/2014 |

* cited by examiner (a)

(b)

(c)

(d)

PRESSURE DETECTION SENSOR AND PRESSURE DETECTION INSOLE INCLUDING SAME

CROSS-REFERENCE TO RELATED PATENT APPLICATIONS

This application is a U.S. National Stage Application under 35 U.S.C. § 371 of PCT Application No. PCT/KR2017/005302, filed May 23, 2017, which claims priority to Korean Patent Application No. 10-2016-0062896, filed May 23, 2016, and Korean Patent Application No. 10-2016-0089287, filed Jul. 14, 2016, whose entire disclosures are hereby incorporated by reference.

TECHNICAL FIELD

The present invention relates to a pressure detecting sensor and a pressure detecting insole including the same, and more particularly, to a sensor and an insole which sense a pressure.

BACKGROUND ART

Recently, due to development of electronic technologies and information and communication technologies, the field of health care has been rapidly developing. That is, a health management system capable of measuring a state of a human body by using biological information is required. For example, a technology of mounting a sensor, which detects a pressure, in a shoe so as to check a health condition, a walking posture, and the like of one who wears the shoe has been developed.

However, when a pressure detecting sensor is built in a sole or an insole of a shoe, a plurality of sensors are necessary, and an additional space is required to insert the sensors therein.

Also, since the sensors do not have flexibility and elasticity, it is difficult to apply the sensors to a shoe having a double curved surface shape and processing time is increased.

Also, there is a noise problem of measuring a pressure at a part other than a part where pressure measurement is desired.

DISCLOSURE

Technical Problem

The present invention is directed to providing a pressure detecting sensor, which detects a pressure according to an applied weight and a position, and a pressure detecting insole.

The present invention is also directed to providing a pressure detecting sensor having improved precision and a pressure detecting insole.

The present invention is also directed to providing a flexible and elastic pressure detecting insole.

The present invention is also directed to providing a pressure detecting sensor having improved durability and manufactured at a low cost and a pressure detecting insole.

Aspects of the present invention are not limited to the above-stated aspects and may include aspects or effects which are recognizable from the following technical solutions or embodiments.

Technical Solution

One aspect of the present invention provides a pressure detecting sensor including an elastic layer comprising a hole and an electrode layer comprising a plurality of electrodes which are arranged to be spaced apart on the elastic layer. Here, the elastic layer comprises a variable member disposed in the hole. The plurality of electrodes are electrically connected by an external pressure. At least one of the plurality of electrodes covers a part of the hole.

The plurality of electrodes may include a first electrode and a second electrode which is disposed to be spaced apart from the first electrode and has a different polarity from that of the first electrode.

The first electrode and the second electrode may include conductive fibers, and the conductive fibers may be metal wires or fibers coated with metal films on surfaces thereof.

An adhesive layer disposed in an area of the electrode layer except an area in which the hole is formed may be included.

An adhesive member disposed to surround the variable member may be included.

A top surface of the variable member may have a step from a top surface of the elastic layer.

The elastic layer may include a plurality of layers.

The variable member may connect the plurality of electrodes which are arranged to be spaced apart due to the external pressure.

An area in which the plurality of electrodes come into contact with a top surface of the elastic layer may be smaller than an area of bottom surfaces of the plurality of electrodes.

Another aspect of the present invention provides a pressure detecting insole including a plurality of pressure detecting sensors and a connector portion connected to the plurality of pressure detecting sensors. Here, each of the pressure detecting sensors includes an elastic layer comprising a hole and an electrode layer comprising a plurality of electrodes arranged to be spaced apart on the elastic layer. The elastic layer includes a variable member disposed in the hole. The plurality of electrodes are electrically connected by an external pressure. At least one of the plurality of electrodes covers a part of the hole.

Advantageous Effects

According to an embodiment of the present invention, a pressure detecting sensor may precisely detect a pressure according to an applied weight and electrodes having a variety of shapes may be manufactured so as to precisely detect pressure distribution. Also, when a pressure detecting insole according to an embodiment of the present invention is used, an additional space for building sensors in a shoe is not necessary.

A pressure detecting insole according to an embodiment of the present invention has high flexibility and elasticity so as to be applicable to shoes having a variety of shapes.

A pressure detecting sensor according to an embodiment of the present invention may prevent noise related to pressure detection from occurring by structurally separating an area of detecting a pressure.

Also, sensitivity of the pressure detecting sensor with respect to an applied pressure may be increased and durability of the pressure detecting sensor may be increased by scattering the pressure.

A pressure detecting sensor according to an embodiment of the present invention may have both a positive polarity and a negative polarity arranged in the same plane such that a thickness of an insole is decreased. Accordingly, a material cost of the pressure detecting sensor is low and processability thereof is excellent.

MODES OF THE INVENTION

Figure 1:
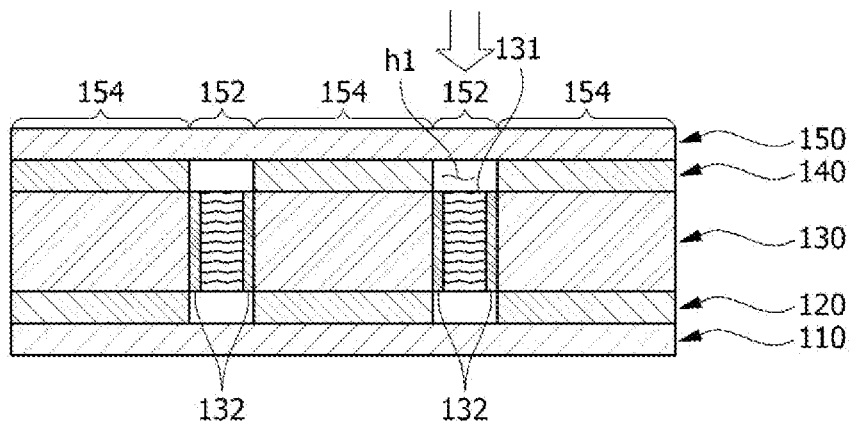
FIG. 1 is a cross-sectional view of a pressure detecting sensor according to one embodiment of the present invention.

Since a variety of modifications and several embodiments of the present invention may be made, exemplary embodiments will be illustrated in the drawings and will be described in detail. However, it should be understood that the present invention is not limited to the exemplary embodiments and includes all changes and equivalents or substitutes included in the concept and technical scope of the present invention.

The terms including ordinal numbers such as "second," "first," and the like may be used for describing a variety of components. However, the components are not limited by the terms. The terms are used only for distinguishing one component from another component. For example, without departing from the scope of the present invention, a second component may be referred to as a first component, and similarly, a first component may be referred to as a second component. The term "and/or" includes any and all combinations of one or a plurality of associated listed items.

When it is described that one component is "connected" or "joined" to another component, it should be understood that the one component may be directly connected or joined to the other component but another component may be present therebetween. On the other hand, when it is described that one component is "directly connected" or "directly joined" to another component, it should be understood that no other component is present therebetween.

Terms used herein are used merely for describing exemplary embodiments and are not intended to limit the present invention. Singular expressions, unless clearly defined otherwise in context, include plural expressions. Throughout the application, it should be understood that the terms "comprise," "have," and the like are used herein to specify the presence of stated features, numbers, steps, operations, elements, components or combinations thereof but do not preclude the presence or addition of one or more other features, numbers, steps, operations, elements, components, or combinations thereof.

Unless defined otherwise, the terms used herein including technical or scientific terms have the same meanings as those which are generally understood by one of ordinary skill in the art. Terms such as those defined in commonly used dictionaries should be construed as having meanings equal to contextual meanings of related art and should not be interpreted in an idealized or excessively formal sense unless defined otherwise herein.

Hereinafter, embodiments will be described in detail with reference to the attached drawings. Regardless of drawing's signs, equal or corresponding elements will be referred to as like reference numerals and an overlapped description thereof will be omitted.

Figure 2:
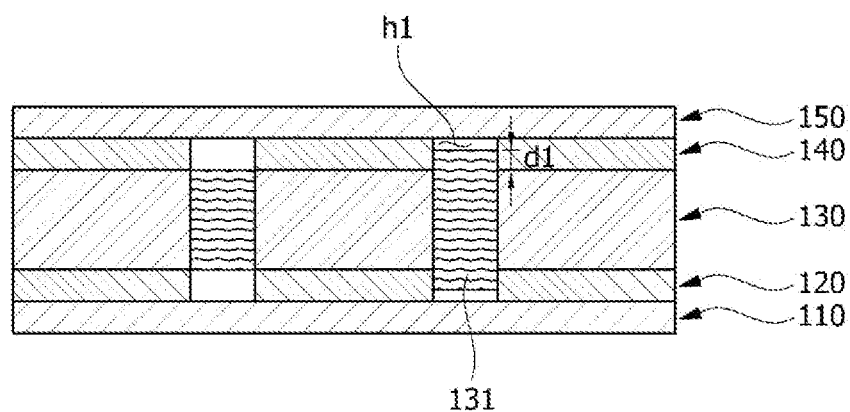
FIGS. 2 and 3 are cross-sectional views illustrating a step formed at the pressure detecting sensor according to one embodiment of the present invention.
Figure 3:
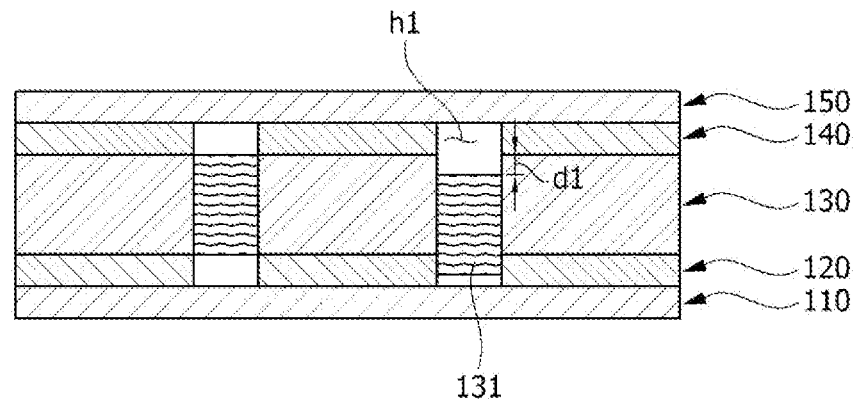

FIG. 1 is a cross-sectional view of a pressure detecting sensor according to one embodiment of the present invention, and FIGS. 2 and 3 are cross-sectional views illustrating a step formed at the pressure detecting sensor according to one embodiment of the present invention.

Referring to FIGS. 1 to 3, a pressure detecting sensor 100 according to one embodiment of the present invention includes a first electrode layer 110, a first adhesive layer 120 disposed on the first electrode layer 110, a first elastic layer 130 disposed on the first adhesive layer 120, a second adhesive layer 140 disposed on the first elastic layer 130, and a second electrode layer 150 disposed on the second adhesive layer 140.

First, the first electrode layer 110 may be formed of fabric. The second electrode layer 150 may also be formed of fabric like the first electrode layer 110.

Also, the first electrode layer 110 and the second electrode layer 150 may have different polarities and be electrically connected. For example, any one of the first electrode layer 110 and the second electrode layer 150 may be grounded. In addition, the first electrode layer 110 and the second electrode layer 150 are formed of layers such that electrodes may be easily grounded and a defective proportion thereof is reduced.

The fabric may include conductive fibers. Here, the conductive fibers may be metal wires or general fibers coated with a metal film on a surface thereof. The conductive fiber may be a general fiber on which metal particles are scattered. When the conductive fiber is a metal wire, a diameter of the metal wire may be 10 µm to 500 µm. When the diameter of the metal wire is less than 10 µm, since strength of the metal wire is too low, it is difficult to process the wire as fabric. When the diameter of the metal wire is more than 500 µm, since strength of the metal wire is too high, flexibility of fabric may decrease such that fabric processing facilities may be damaged during processing, and a user may easily feel a sensation of difference.

Here, the metal wire may be Cu, Ni, or a stainless alloy. The stainless alloy may be, for example, a martensite-based stainless alloy, a ferrite-based stainless alloy, an austenite-based stainless alloy, a diphase stainless alloy, a precipitation-hardened stainless alloy, or the like. When the metal wire is a stainless alloy, an anticorrosion property of the pressure detecting sensor 100 may be increased.

When the conductive fiber is a general fiber coated with a metal film on a surface thereof, the metal film may be formed using a method of coating the surface of the general fiber with metal particles through plating or deposition. Here, the metal particles may be Cu, Ni, or a stainless alloy, and a thickness of the metal film may be 1 μm to 50 μm. When the thickness of the metal film is less than 1 μm, since conductivity is low, a loss may occur during signal transmission. When the thickness of the metal film is more than 50 μm, the metal film may easily fall off of the surface of the fiber.

The first adhesive layer 120 may be disposed in an area on the first electrode layer 110 except for an area in which a first hole h1 of the first elastic layer 130 is formed. Hereinafter, an area in which a first variable member 131 is formed is a sensing area 152 and is described as an area capable of sensing a pressure. Also, an area excluding the sensing area 152 is described as a non-sensing area 154.

Also, the first adhesive layer 120 may have a variety of sizes and shapes between the first elastic layer 130 and the first electrode layer 110.

As an example, the first adhesive layer 120 may have a structure in which both sides of a film are coated with an insulating adhesive. Hereupon, the first electrode layer 110 and the first elastic layer 130 may be combined therewith. Also, a part disposed below the sensing area 152 may be punched or may not be coated with an insulating adhesive. As another example, the first adhesive layer 120 has a structure in which both sides of a film are coated with an adhesive and additionally coated with an insulating material excluding an area disposed below the sensing area 152.

The first elastic layer 130 may be disposed on the first adhesive layer 120 and may include a plurality of such first holes h1 formed therein. Also, the first elastic layer 130 may include an elastic body. Here, the elastic body may be a fabric material having a random fabric arrangement such as foam, non-woven fabric, a nanoweb, and the like, a synthetic fiber including one selected from the group consisting of polyurethane, nylon, polyethylene terephthalate, and polyester, a natural fiber, an elastomer, rubber, urethane, or the like.

Also, the first variable member 131 may be disposed in the first hole h1 formed in the first elastic layer 130. As an example, the first hole h1 may be a through hole, but the present invention is not limited thereto.

The first variable member 131 may include an elastic body like the first elastic layer 130.

Here, the elastic body may be a fabric material having a random fabric arrangement such as foam, non-woven fabric, a nanoweb, and the like, a synthetic fiber including one selected from the group consisting of polyurethane, nylon, polyethylene terephthalate, and polyester, a natural fiber, an elastomer, rubber, urethane, or the like.

Meanwhile, a conductive compound included in the first variable member 131 may be applied to the surface of the fibers which form the elastic body or may be scattered in the elastic body. Due to the above configuration, when a pressure is applied to the first variable member 131 which is the sensing area 152, the first variable member 131 may physically change. For example, when an external pressure is applied, the variable member 131 disposed below the sensing area 152 may have a thickness which is decreased and a resistance which is changeable.

In detail, when a pressure is applied to the sensing area 152, the first electrode layer 110, the variable member 131, and the second electrode layer 150 may be electrically connected. Also, the thickness and resistance of the first variable member 131 may change, and a level of an electrical signal which flows between the first electrode layer 110 and the second electrode layer 150 may change due to the change in resistance. The intensity of pressure applied to the sensing area 152 may be sensed using the change in the level of the electrical signal.

That is, pressure sensing with respect to the pressure applied to the sensing area 152 may be performed through the first variable member 131 disposed below the sensing area 152. In addition, an electrical signal is transmitted to the first variable member 131 disposed below the sensing area 152 to which a pressure is applied, and an electrical signal is not transmitted to the first variable member 131 disposed below the sensing area 152 to which a pressure is not applied.

This is because an electrical signal is structurally blocked from being transmitted from the first variable member 131 to the first elastic layer 130 adjacent to the first variable member 131. That is, the sensing area 152 and the non-sensing area 154 may be structurally separated from each other so as to prevent noise. Accordingly, a signal, from which noise that is an electrical signal sensed in an area to which a pressure is not applied is removed, may be obtained.

Here, the conductive compound may include conductive polymers and conductive powder. The conductive compound may be included at 1 to 10 wt % of the elastic body. When the conductive compound is included by more than 10 wt % of the elastic body, it is difficult to secure an insulation property in a state in which a pressure is not applied. Here, the conductive polymers may include polyaniline or polypyrrole. Also, the conductive powder may include one selected from the group consisting of Au, Ag, Cu, Ni, carbon nano tubes (CNT), graphene, and a ceramic filler.

The conductive powder may have a diameter of 10 nm to 500 μm and may have a spherical shape, a needle shape, or a plate shape. When the diameter of the conductive powder is less than 10 nm, resistance of the entire first variable member 131 is decreased due to poor dispersion in the conductive powder and high resistance at an interface between particles. Also, when the diameter of the conductive power is more than 500 μm, a frictional force increases due to an uneven surface of the first variable member 131 such that processing may be difficult.

Also, a step may be formed between a top surface of the first variable member 131 and a top surface of the first elastic layer 130. As an example, as shown in FIG. 2, the top surface of the first variable member 131 may be disposed above the top surface of the first elastic layer 130 so as to form a step d1. Like the top surface of the first variable member 131, a step may be formed between a bottom surface of the first variable member 131 and a bottom surface of the first elastic layer 130.

Hereby, the first electrode layer 110 and the second electrode layer 150 may be easily electrically connected to the first variable member 131 due to the pressure applied to the sensing area 152. Also, a pressure may be intensively collected on a thickness of the first variable member 131 which protrudes as much as the step d1. Accordingly, a low pressure applied to the sensing area 152 may be sensed.

As shown in FIG. 3, the top surface of the first variable member 131 may be disposed below the top surface of the first elastic layer 130 so as to form a step d2. A step may be formed between the bottom surface of the first variable member 131 and the bottom surface of the first elastic layer 130.

Accordingly, the pressure applied to the sensing area 152 is primarily distributed to the first elastic layer 130 in contact with the first variable member 131 and is finally transmitted to the first variable member 131. That is, durability of the first variable member 131 may be improved through pressure distribution.

Also, a first adhesive member 132 is disposed on a surface of the first elastic layer 130 with which the first hole h1 and the first variable member 131 come into contact so as to fix and support the first variable member 131.

The second adhesive layer 140 may be disposed in an area of the first elastic layer 130 in which the first hole h1 is not formed. The second adhesive layer 140 may be applied like the first adhesive layer 120.

The second electrode layer 150 may be disposed on the second adhesive layer 140 and may have a different polarity from that of the first electrode layer 110. Also, the second electrode layer 150 may be formed of fabric like the first electrode layer 110. Also, as described above, a pressure may be sensed from an electrical signal which flows through the second electrode layer 150, the first variable member 131, and the first electrode layer 110 disposed below the sensing area 152.

Figure 4:
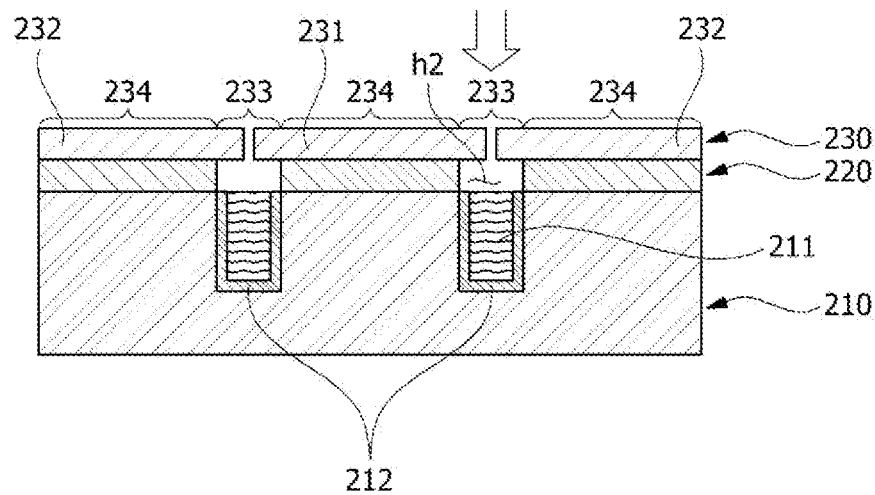
FIG. 4 is a cross-sectional view of a pressure detecting sensor according to another embodiment of the present invention.
Figure 5:
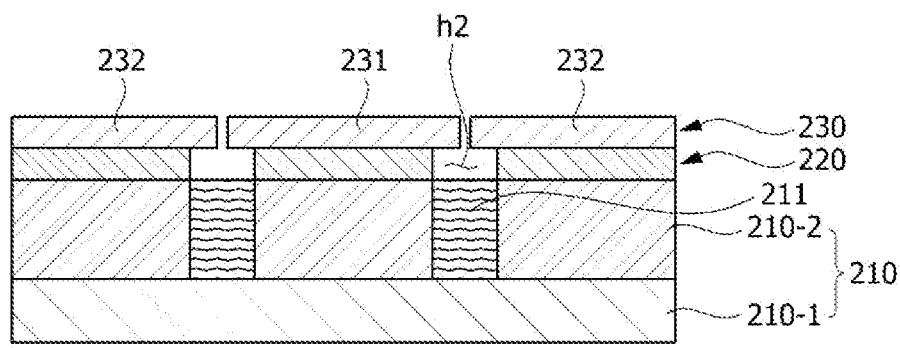
FIG. 5 is a view illustrating an elastic layer including a plurality of layers in the pressure detecting sensor according to another embodiment of the present disclosure.
Figure 6:
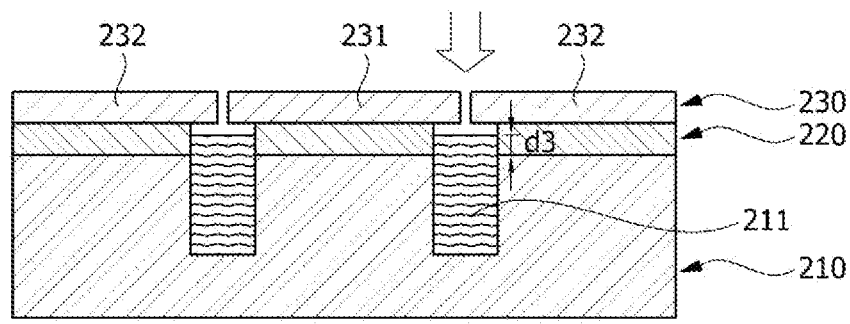
FIGS. 6 and 7 are cross-sectional views illustrating a step formed at the pressure detecting sensor according to another embodiment of the present invention.
Figure 7:
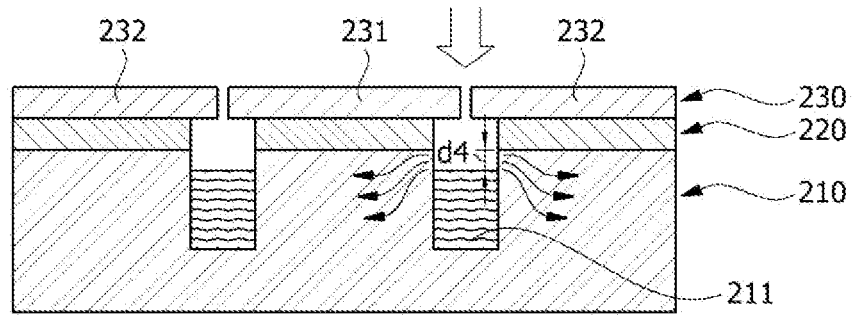

FIG. 4 is a cross-sectional view of a pressure detecting sensor according to another embodiment of the present invention, FIG. 5 is a view illustrating an elastic layer including a plurality of layers in the pressure sensor according to another embodiment of the present disclosure, and FIGS. 6 and 7 are cross-sectional views illustrating a step formed at the pressure sensor according to another embodiment of the present invention.

Referring to FIGS. 4 to 7, a pressure detecting sensor 200 according to another embodiment of the present invention may include a second elastic layer 210 including a second hole, a third adhesive layer 220 disposed above the second elastic layer 210, and a third electrode layer 230 disposed on the third adhesive layer 220.

The second elastic layer 210 may include an elastic body like the above-described first elastic layer. Here, the elastic body may be a fabric material having a random fabric arrangement such as foam, non-woven fabric, a nanoweb, and the like, a synthetic fiber including one selected from the group consisting of polyurethane, nylon, polyethylene terephthalate, and polyester, a natural fiber, an elastomer, rubber, urethane, or the like.

Also, a second variable member 211 may be disposed in the second hole h2 formed in the second elastic layer 210. The second variable member 211 may include an elastic body like the second elastic layer 210. Also, the second variable member 211 may include a conductive compound distributed in the elastic body.

Here, the elastic body may be a fabric material having a random fabric arrangement such as foam, non-woven fabric, a nanoweb, and the like, a synthetic fiber including one selected from the group consisting of polyurethane, nylon, polyethylene terephthalate, and polyester, a natural fiber, an elastomer, rubber, urethane, or the like.

Meanwhile, the conductive compound included in the second variable member 211 may be applied to a surface of the fibers which form the elastic body or may be scattered in the elastic body. Accordingly, when a physical change occurs, that is, when a pressure is applied to the second variable member 211 that is a sensing area 233, a thickness of the second variable member 211 disposed below the sensing area 233 is reduced and resistance thereof changes. Hereinafter, an area in which the second variable member 211 is formed is the sensing area 233 is described as an area capable of sensing a pressure. Also, an area excluding the sensing area 233 is explained as a non-sensing area 234. In detail, when the pressure is applied to the sensing area 233, a plurality of electrodes 231 and 232 disposed to be spaced apart from the third electrode layer 230 are electrically connected to the second variable member 211. According to the change in resistance of the second variable member 211, a pressure applied to the sensing area 233 may be sensed through a change in a level of an electrical signal between the plurality of electrodes 231 and 232 of the third electrode layer 230 according to the change in resistance of the second variable member 211.

That is, pressure sensing with respect to the pressure applied to the sensing area 233 may be performed through the second variable member 211 disposed below the sensing area 233. In addition, an electrical signal is transmitted to the second variable member 211 disposed below the sensing area 233 to which a pressure is applied, and an electrical signal is not transmitted to the second variable member 211 disposed below an area except the sensing area 233 to which a pressure is not applied.

That is, the sensing area 233 and the non-sensing area 234 may be structurally separated from each other so as to prevent noise. This is because since the second elastic layer 210 surrounds the second variable member 211 to which a pressure is applied, a path through which an electrical signal is transmitted to the adjacent second variable member is blocked by the second elastic layer 210. Accordingly, a signal, from which noise that is an electrical signal sensed in an area to which a pressure is not applied is removed, may be obtained.

Here, the conductive compound may include conductive polymers and conductive powder. The conductive compound may be included at 1 to 10 wt % of the elastic body. When the conductive compound is included by more than 10 wt % of the elastic body, it is difficult to secure an insulation property in a state in which a pressure is not applied. Here, the conductive polymers may include polyaniline or polypyrrole. Also, the conductive powder may include one selected from the group consisting of Au, Ag, Cu, Ni, CNT, graphene, a ceramic filler.

Here, the conductive powder may have a diameter of 10 nm to 500 μm and may have a spherical shape, a needle shape, or a plate shape. When the diameter of the conductive powder is less than 10 nm, resistance of the entire second variable member 211 is decreased due to poor dispersion in the conductive powder and high resistance at an interface between particles. Also, when the diameter of the conductive power is more than 500 μm, a frictional force increases due to an uneven surface of the second variable member 211 such that processing may be difficult.

Referring to FIG. 5, the second elastic layer 210 may have a shape in which a plurality of layers are stacked. As an example, the second elastic layer 210 may include a second lower elastic layer 210-1 and a second upper elastic layer 210-2. Also, an elastic force of the second upper elastic layer 210-2 may be greater than an elastic force of the second lower elastic layer 210-1. Hereby, the pressure detecting sensor 200 which secures flexibility and has an improved support force may be provided.

Also, a step may be formed between a top surface of the second variable member 211 and a top surface of the second elastic layer 210. As an example, referring to FIG. 6, the top surface of the second variable member 211 may be disposed above the top surface of the second elastic layer 210 so as to form a step d3. Hereby, the plurality of electrodes 231 and 232 of the third electrode layer 230 disposed above the second variable member 211 may be easily electrically connected to the second variable member 211 due to the pressure applied to the sensing area 233. Also, a pressure may be intensively collected on a thickness of the second variable member 211 which protrudes as much as the step d3. Accordingly, it is possible to sense even a low pressure applied to the sensing area 233.

As shown in FIG. 7, the top surface of the second variable member 211 may be disposed below the top surface of the second elastic layer 210 so as to form a step d4. Accordingly, the pressure applied to the sensing area 233 may be primarily distributed to the second elastic layer 210 in contact with the second variable member 211 and may be finally transmitted to the second variable member 211. That is, durability of the second variable member 211 may be improved.

A second adhesive member 212 may be disposed on the second elastic layer 210 to surround the second variable member 211. That is, the second adhesive member 212 may be disposed on a surface on which the second variable member 211 and the second hole h2 come into contact with each other.

The third adhesive layer 220 may have the same material as that of the first adhesive layer as described above. Accordingly, the third adhesive layer 220 may be combined with the third electrode layer 230 disposed on a top surface of the third adhesive layer 220.

The third electrode layer 230 may include the plurality of electrodes 231 and 232. As an example, the plurality of electrodes 231 and 232 may include a first electrode 231 and a second electrode 232. Also, the first electrode 231 and the second electrode 232 may be disposed to be spaced apart and may have different polarities. For example, the first electrode 231 may be a negative electrode and the second electrode 232 may be a positive electrode.

Also, an area in which the plurality of electrodes 231 and 232 come into contact with the top surface of the second elastic layer 210 or the top surface of the third adhesive layer 220 may be smaller than an area of the bottom surfaces of the plurality of electrodes 231 and 232.

Also, at least one of the first electrode 231 and the second electrode 232 may cover a part of the second hole h2. As an example, the first electrode 231 and the second electrode 232 may cover the second hole h2 by the same rate. In addition, only one of the first electrode 231 and the second electrode 232 may cover the second hole h2.

Accordingly, when a small pressure is applied to the sensing area 233 of the pressure detecting sensor 200 according to one embodiment, even though a thickness of the second variable member 211 slightly changes, the second variable member 211 may be electrically connected to an adjacent electrode disposed to be spaced apart. That is, a range of pressure detection may be extended.

Figure 8:
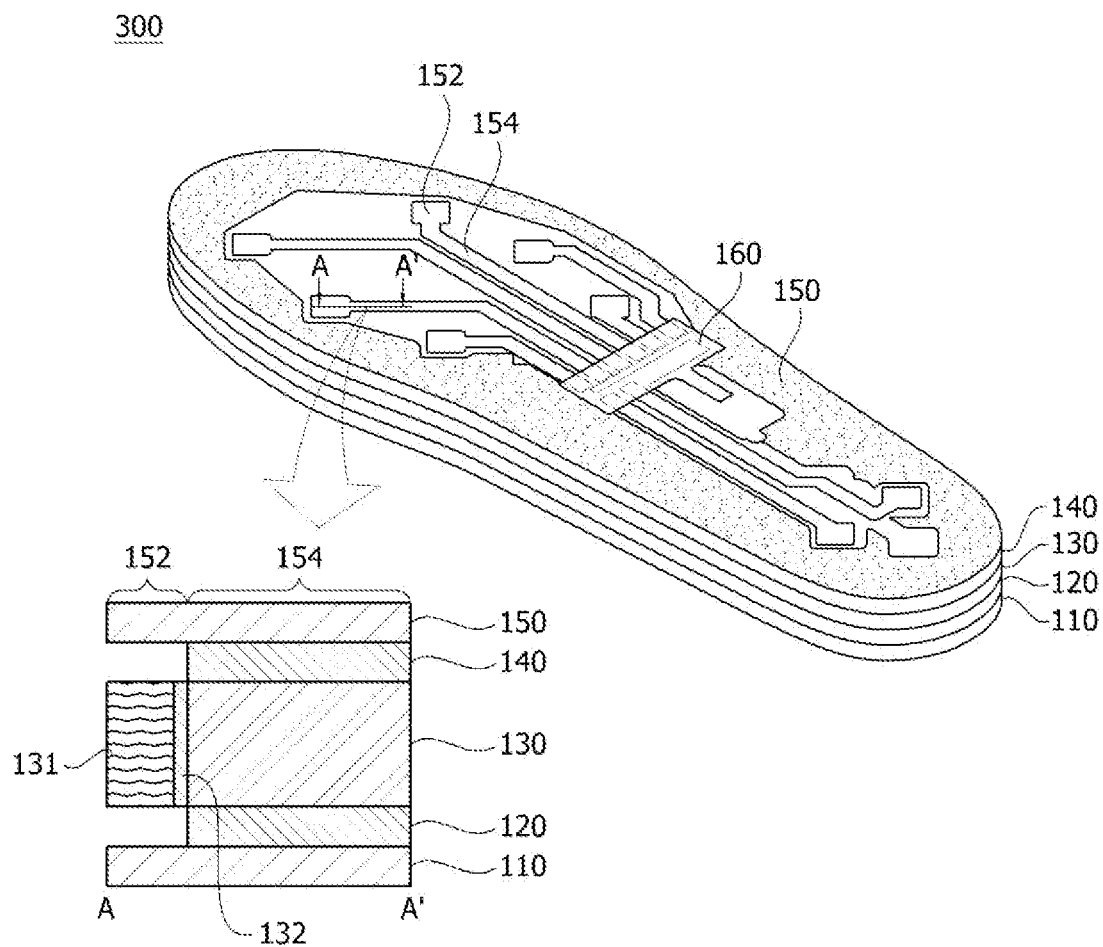
FIG. 8 is a perspective view illustrating a pressure detecting insole according to one embodiment of the present invention.

FIG. 8 is a perspective view illustrating a pressure detecting insole according to one embodiment of the present invention. Referring to FIG. 8, a pressure detecting insole 300 according to one embodiment may include a plurality of pressure detecting sensors and a connector portion 160 connected to the pressure detecting sensors.

Also, the pressure detecting insole 300 may have a shape including the above-described plurality of pressure detecting sensors in which the plurality of layers of the pressure detecting sensor described above with reference to FIGS. 1 to 3 extend. Also, like a cross section A-A, the sensing area 152 in which the first variable member 131 of the pressure detecting sensor is disposed may be formed at a part of the pressure detecting insole 300 where sensing of a pressure is needed. Also, the non-sensing area 154, which is an area excluding the sensing area 152, may be an area which transmits an electrical signal sensed in the sensing area 152 to the connector portion 160 as shown in FIG. 8. The connector portion 160 may be embodied as a flexible printed circuit board (FPCB) and may be connected to an external device (not shown).

Figure 9:
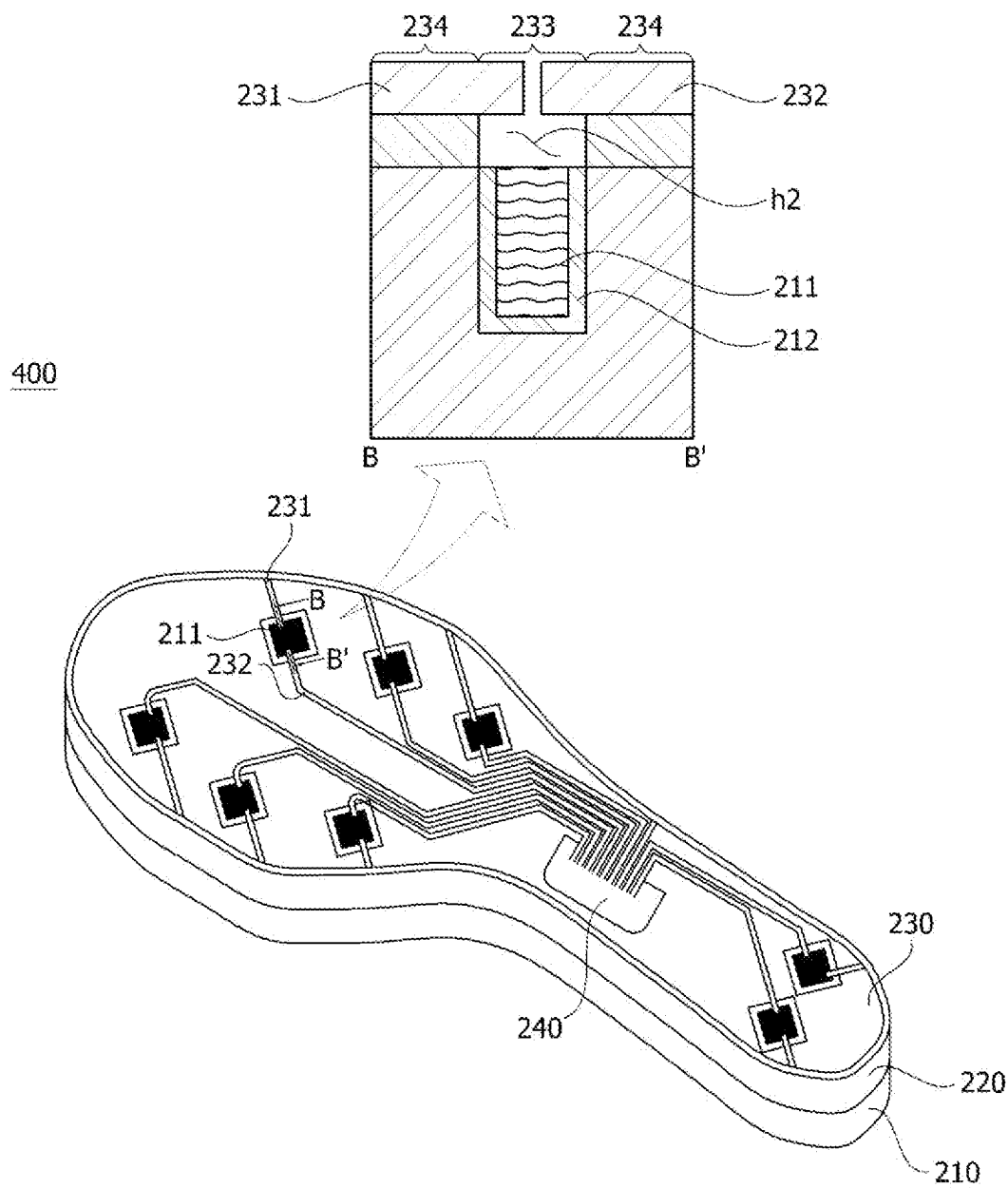
FIG. 9 is a perspective view illustrating a pressure detecting insole according to another embodiment of the present invention.

FIG. 9 is a perspective view illustrating a pressure detecting insole according to another embodiment of the present invention. Referring to FIG. 9, a pressure detecting insole 400 according to another embodiment may include a plurality of pressure detecting sensors and a connector portion 240 connected to the pressure detecting sensors.

The pressure detecting insole 400 may have a shape including the plurality of pressure detecting sensors in which the plurality of layers of the pressure detecting sensor described above with reference to FIGS. 4 to 7 extend. Also, a part in which the plurality of electrodes 231 and 232 are not disposed may be present in the third electrode layer 230. Also, like a cross section B-B, the sensing area 233 in which the second variable member 211 of the pressure detecting sensor is disposed may be formed at a part of the pressure detecting insole 400 where sensing of a pressure is needed. Also, the non-sensing area 234, which is an area excluding the sensing area 233, may be an area which transmits an electrical signal sensed in the sensing area 233 to the connector portion 240 like the above description. The connector portion 240 may be embodied as an FPCB and may be connected to an external device (not shown) as described above.

Also, although the pressure detecting insole including the pressure detecting sensors has been described above, the pressure detecting insole may be applied to a case of measuring a pressure to a wearable product such as gloves, a belt, a mat, and the like.

Figure 10:
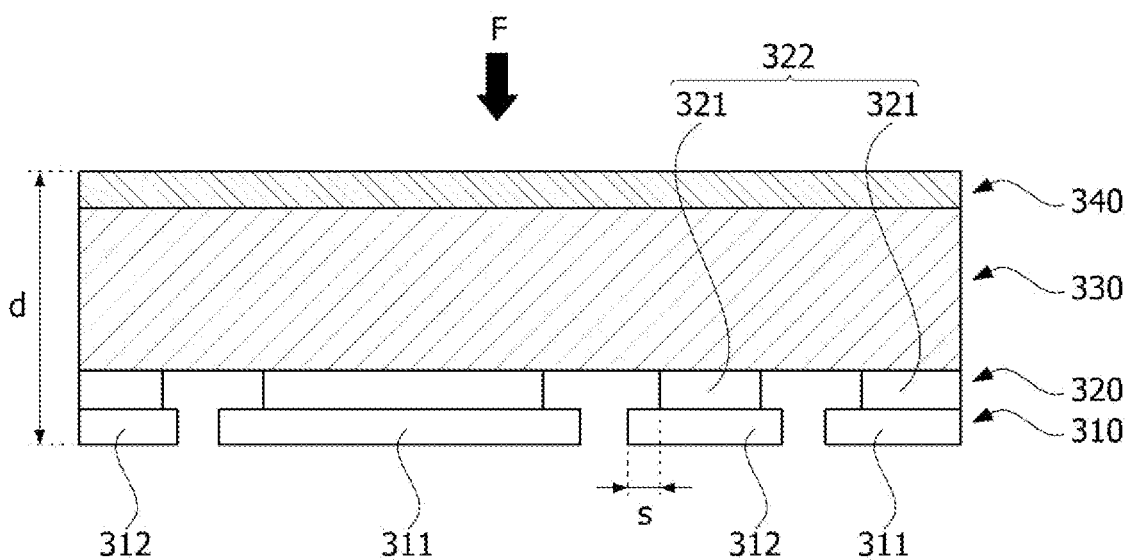
FIG. 10 is a cross-sectional view of a pressure detecting sensor according to still another embodiment of the present invention.
Figure 11:
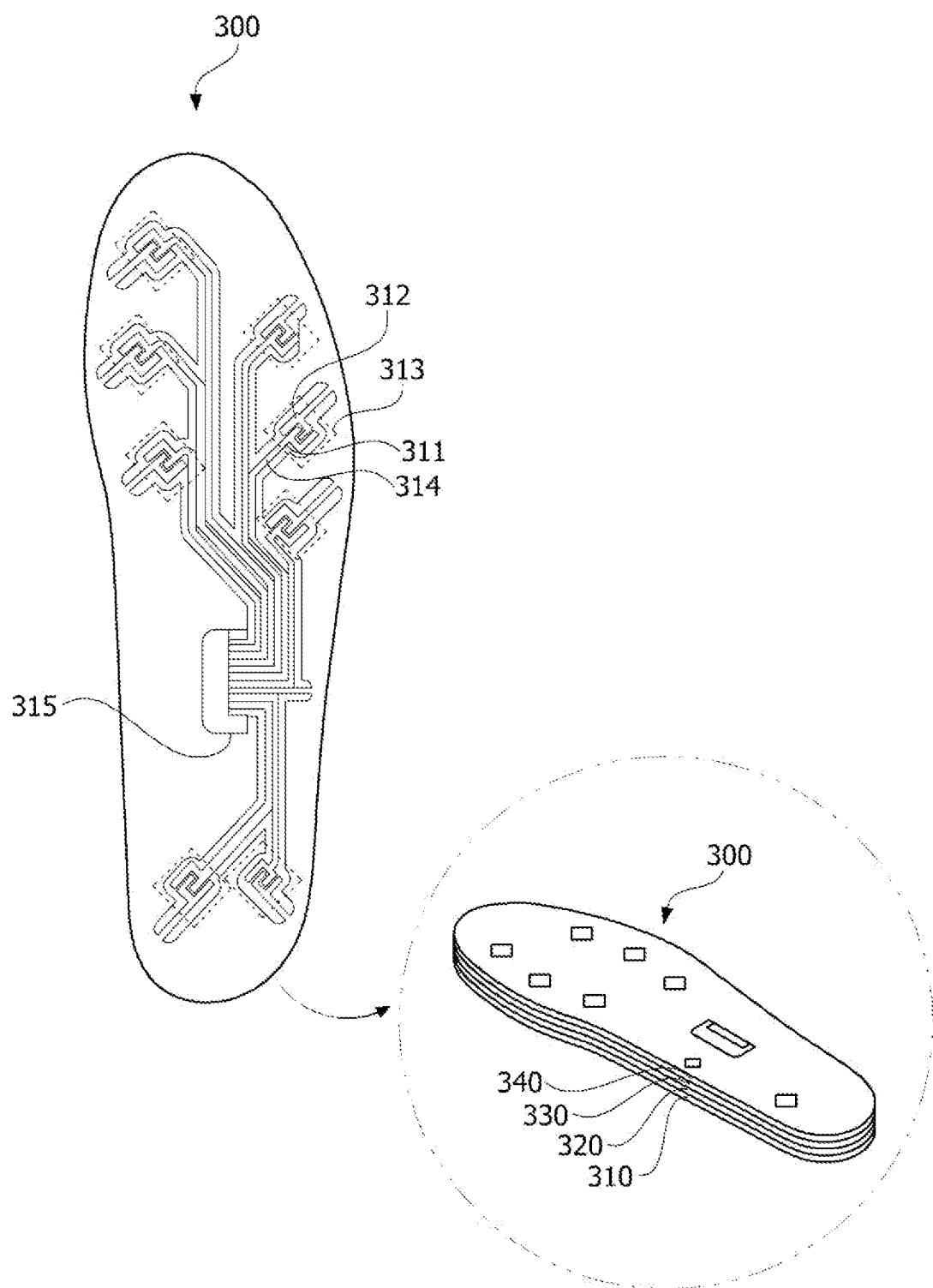
FIG. 11 is a perspective view of a pressure detecting insole according to yet another embodiment of the present invention.
Figure 12:
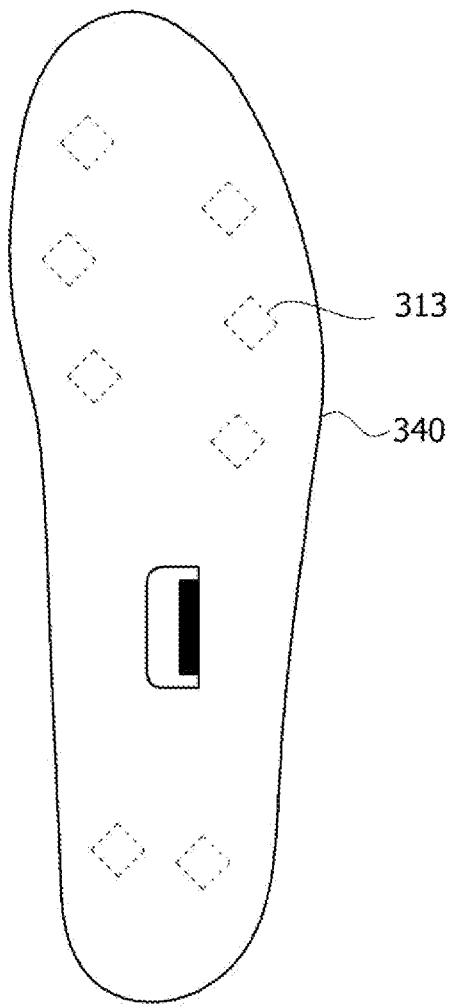
FIG. 12 is a top view of the pressure detecting insole according to yet another embodiment of the present invention.

FIG. 10 is a cross-sectional view of a pressure detecting sensor according to still another embodiment of the present invention, FIG. 11 is a perspective view of a pressure detecting insole according to still another embodiment of the present invention, and FIG. 12 is a top view of a pressure detecting insole according to yet another embodiment of the present invention.

Referring to FIGS. 10 to 12, the pressure detecting sensor and the pressure detecting insole 300 may include an electrode layer 310, a connecting layer 320, a third elastic layer 330, and a cover layer 340.

The pressure detecting insole 300 includes the pressure detecting sensor in a sensing area 313 which senses a pressure and includes a plurality of layers including the electrode layer 310, the connecting layer 320, the third elastic layer 330, and the cover layer 340.

The electrode layer 310 may be formed with fabric and includes the first electrode 311 and the second electrode 312. Also, the first electrode 311 and the second electrode 312 of the electrode layer 310 may be arranged to be spaced apart in the same plane. Accordingly, grounded connection may be possible on one layer and it is unnecessary to install an additional ground electrode such that material costs and manufacturing costs of the pressure detecting insole 300 are reduced. Further, a thickness d of the pressure detecting insole 300 is also reduced. In addition, it becomes easy to ground an electrode such that a defective proportion thereof is reduced.

The fabric may include conductive fibers. Here, the conductive fibers may be metal wires or general fibers coated with a metal film on a surface thereof. The conductive fiber may be a general fiber on which metal particles are scattered. When the conductive fiber is a metal wire, a diameter of the metal wire may be 10 µm to 500 µm. When the diameter of the metal wire is less than 10 µm, since strength of the metal wire is too low, it is difficult to process the wire as fabric. When the diameter of the metal wire is more than 500 µm, since strength of the metal wire is too high, flexibility of fabric may decrease such that fabric processing facilities may be damaged during processing and a user may easily feel a sensation of difference.

Here, the metal wire may be Cu, Ni, or a stainless alloy. The stainless alloy may be, for example, a martensite-based stainless alloy, a ferrite-based stainless alloy, an austenite-based stainless alloy, a diphase stainless alloy, a precipitation-hardened stainless alloy, or the like. When the metal wire is a stainless alloy, an anticorrosion property of the pressure detecting insole 300 may be increased.

When the conductive fiber is a general fiber coated with a metal film on a surface thereof, the metal film may be formed using a method of coating the surface of the general fiber with metal particles through plating or deposition. Here, the metal particles may be Cu, Ni, or a stainless alloy, and a thickness of the metal film may be 1 µm to 50 µm. When the thickness of the metal film is less than 1 µm, since conductivity is low, a loss may occur during signal transmission. When the thickness of the metal film is more than 50 µm, the metal film may easily fall off of the surface of the fiber.

The connecting layer 320 may include an insulating material 321 and may be disposed on the electrode layer 310. In detail, the insulating material 321 may be disposed between the first electrode 311 and the second electrode 312 of the electrode layer 310 and the third elastic layer 330.

Also, the insulating material 321 may be spaced apart from the first electrode 311 and the second electrode 312 so as to form a pair of insulating materials 322. Also, the insulating material 321 may have a structure in which both sides of a film are coated with an insulating adhesive. Also, the first electrode 311 and the second electrode 312 may be any one of a positive electrode and a negative electrode.

As an embodiment, the sensing area 313 is an area in which a pressure detecting sensor is disposed and which includes a gap between the first electrode 311 and the second electrode 312 and senses an externally applied pressure. The electrode layer 310 in the pressure detecting insole 300 includes the sensing area 313.

The sensing area 313 may be disposed at a place to sense a pressure thereof and may more precisely recognize a state of a foot of a user by sensing the pressure at the place where the state of the foot is desired to be known.

Referring to FIG. 12, when a pressure F is applied to the sensing area 313, a thickness of the third elastic layer 330, which has elasticity, is changed. Here, due to the change in the thickness of the third elastic layer 330, the first electrode 311 and the second electrode 312 which are spaced apart from each other are connected so as to be electrified. Also, a degree of pressure is sensed from a generated electrical signal.

In the pressure detecting insole 300 according to still another embodiment of the present invention, the first electrode 311 and the second electrode 312 are disposed to be spaced apart and an insulating body is also disposed to be spaced part on the first electrode 311 and the second electrode 312 such that a pressure may be sensed by forming not only the gap between the first electrode 311 and the second electrode 312 but also a gap between a pair of insulating bodies 322 and the insulating body 322.

Also, an area in which the insulating body 321 and the first electrode 311 come into contact with each other may be formed to be smaller than an area of a top surface of the first electrode 311. A certain gap s may be formed between one end of the first electrode 311 and one end of the insulating body.

Also, an area in which the insulating body 321 and the second electrode 312 come into contact with each other may be formed to be smaller than an area of a top surface of the second electrode 312. A certain gap s may be formed between one end of the first electrode 311 and one end of the insulating body 321.

Accordingly, when a low pressure is applied to the pressure detecting insole 300 according to still another embodiment, even though the thickness of the third elastic layer 330 is slightly changed, the third elastic layer 330 may electrically connect the first electrode and the second electrode 312 at a gap between the pair of insulating bodies 322. That is, a range of pressure detection may be extended.

As yet another embodiment, the non-sensing area 314 is a wire electrically connected to the first electrode 311 and the second electrode 312 in the same plane and may be an area excluding the sensing area 313. Also, the non-sensing area 314 transmits an electrical signal generated by the sensing area 313 to a connector 315. Here, the connector 315 may be embodied as an FPCB and may be connected to an external device (not shown).

The external device may analyze body pressure distribution of a user applied to the pressure detecting insole 300 by using the electrical signal received through the connector 315. Here, the connector 315 to which the first electrode 311 and the second electrode 312 are connected may be formed in the same plane with the first electrode 311 and the second electrode 312.

Also, in the non-sensing area 314, the insulating body 321 may be disposed between the third elastic layer 330 and the electrode to be insulated. Due to disposition of the insulating body, the pressure detecting insole 300 according to yet another embodiment does not sense a pressure applied to the non-sensing area 314 and senses only a pressure applied to the sensing area 313 in which the pressure detecting sensor is located and the gap is formed between the first electrode 311 and the second electrode 312 to sense a pressure.

Meanwhile, the third elastic layer 330 may include an elastic body and a conductive compound dispersed in the elastic body. Here, the elastic body may be a fabric material having a random fabric arrangement such as foam, non-woven fabric, a nanoweb, and the like, a synthetic fiber including one selected from the group consisting of polyurethane, nylon, polyethylene terephthalate, and polyester, a natural fiber, an elastomer, rubber, urethane, or the like.

Accordingly, the third elastic layer 330 includes micro air holes and has elasticity. Here, the thickness of the third elastic layer 330 may be 1 to 4 mm. When the thickness of the third elastic layer 330 is less than 1 mm, it may be difficult to maintain an insulation function in a normal state, that is, a state in which an external force is not applied, and a change in resistance may be small because the change in thickness is small when an external force is applied. Accordingly, pressure sensing efficiency may be decreased. When the thickness of the third elastic layer 330 exceeds 4 mm, it is difficult to apply the third elastic layer to an inside of a shoe.

Meanwhile, the conductive compound included in the third elastic layer 330 may be applied to a surface of the fibers which form the elastic body or may be scattered in the elastic body. Accordingly, the third elastic layer 330 has an insulating property in which resistance is greater than or equal to 1 in a normal state. However, when a physical changes occurs around the third elastic layer 330, that is, when a pressure is applied to the sensing area 313, the thickness of the third elastic layer 330 disposed below the sensing area 313 is decreased such that resistance is changed.

Here, the conductive compound may include conductive polymers and conductive powder. The conductive compound may be included at 1 to 10 wt % of the elastic body. When the conductive compound is included by more than 10 wt % of the elastic body, it is difficult to secure an insulation property in a state in which a pressure is not applied.

Here, the conductive polymers may include polyaniline or polypyrrole. Also, the conductive powder may include one selected from the group consisting of Au, Ag, Cu, Ni, CNT, graphene, and a ceramic filler.

Here, the conductive powder may have a diameter of 10 nm to 500 μm and may have a spherical shape, a needle shape, or a plate shape. When the diameter of the conductive powder is less than 10 nm, resistance of the entire third elastic layer 330 is decreased due to poor dispersion in the conductive powder and high resistance at an interface between particles. Also, when the diameter of the conductive power exceeds 500 μm, a frictional force increases due to an uneven surface of the third elastic layer 330 such that processing may be difficult. Also, the third elastic layer 330 may have a shape in which a plurality of layers are stacked.

The cover layer 340 surrounds an outer surface of the pressure detecting insole 300 and protects the pressure detecting insole 300 from an external shock.

Figure 13:
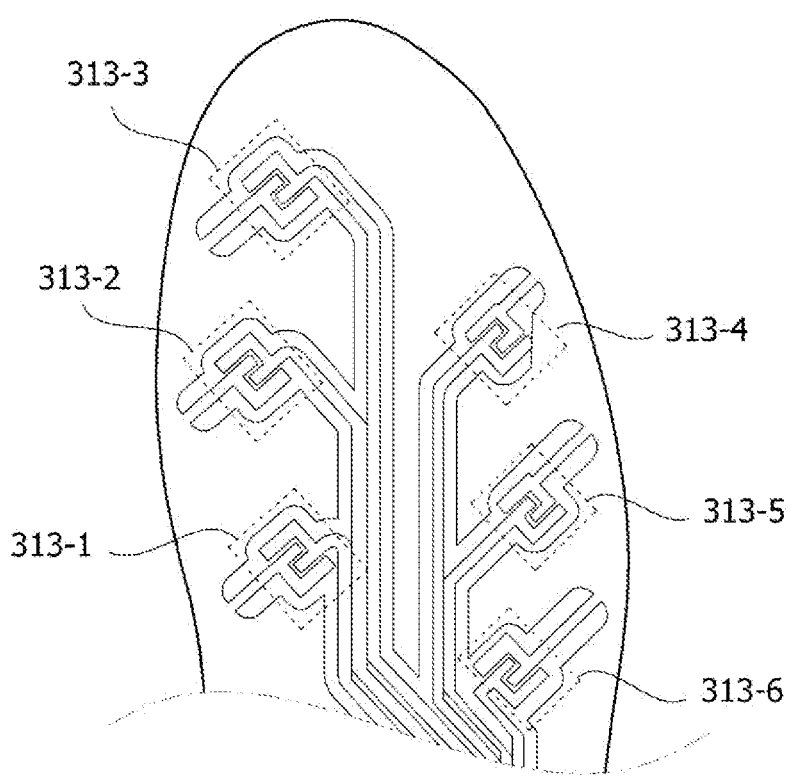
FIG. 13 is a partial bottom view of the pressure detecting insole according to yet another embodiment of the present invention.

FIG. 13 is a partial bottom view of a pressure detecting insole according to yet another embodiment of the present invention. Referring to FIG. 13, as an example, sensing areas 313-1 to 313-6 may be distributed into six parts.

Also, as measuring conditions, the first electrode and the second electrode having a variety of shapes are formed by etching electrode layers which are conductive fabric coated with metal films such that the sensing area and the non-sensing area are formed in the pressure detecting insole. Accordingly, although the conductive fabric has uniform linear resistance, in etching, an etching operation is not uniformly performed due to fabric properties. Due to this, initial resistance is shown to be different according to each position in the sensing area.

Also, a slight error is present before/after repetitive bending at a measuring position at which linear resistance is measured such that the slight error is included in a result of measuring linear resistance after performing repetitive bending.

First, when the first electrode and the second electrode are horizontally arranged in the same plane, 250,000 instances of repetitive bending of the sensing areas 313-1 to 313-6 are performed and a change ratio of linear resistance to initial linear resistance of the electrode layer was measured (refer to Table 1).

TABLE 1

| Measurement position | Initial resistance [/cm] | After repetitive bending [/cm] (250,000) | A change ratio in comparison to initial stage [%] |
|---|---|---|---|
| 313-1 | 6.625 | 3.38 | 51 |
| 313-2 | 3.43 | 3.47 | 101 |
| 313-3 | 2.39 | 2.88 | 321 |
| 313-4 | 0.61 | 0.71 | 117 |

TABLE 1-continued

| Measurement position | Initial resistance [/cm] | After repetitive bending [/cm] (250,000) | A change ratio in comparison to initial stage [%] |
|---|---|---|---|
| 313-5 | 4.94 | 3.82 | 77 |
| 313-6 | 0.63 | 0.94 | 150 |
| Mean change ratio in comparison to initial stage | | | 103% |

In addition, when the first electrode and the second electrode were vertically arranged in the sensing area instead of horizontally (a structure in which the third elastic layer is formed between the first electrode and the second electrode), 250,000 instances of repetitive bending of the sensing areas 313-1 to 313-6 were performed and a change ratio of linear resistance to initial linear resistance of the electrode layers was measured (refer to Table 2).

TABLE 2

| Measurement position | Initial resistance [/cm] | After repetitive bending [/cm] (250,000) | A change ratio in comparison to initial stage [%] |
|---|---|---|---|
| 313-1 | 0.313 | 0.719 | 230 |
| 313-2 | 1.04 | 4.09 | 395 |
| 313-3 | 0.29 | 2.07 | 715 |
| 313-4 | 0.20 | 1.74 | 850 |
| 313-5 | 0.29 | 0.912 | 310 |
| 313-6 | 0.313 | 0.313 | 300 |
| Mean change ratio in comparison to initial stage | | | 433% |

Referring to Table 1 and Table 2, since change in linear resistance is less when the first electrode and the second electrode are horizontally arranged in the same plane to be spaced apart and a pressure is sensed than when the first electrode and the second electrode are vertically arranged and a pressure is sensed, it is shown that durability of the pressure detecting insole is greatly improved when the first electrode and the second electrode are horizontally arranged to be spaced apart.

Such a result may be seen through a difference in mean ratio of change in comparison to initial linear resistance. Also, wrinkles are not generated by repetitive bending when the first electrode and the second electrode are horizontally arranged. However, wrinkles are generated by repetitive bending when the first electrode and the second electrode are vertically arranged.

Figure 14:
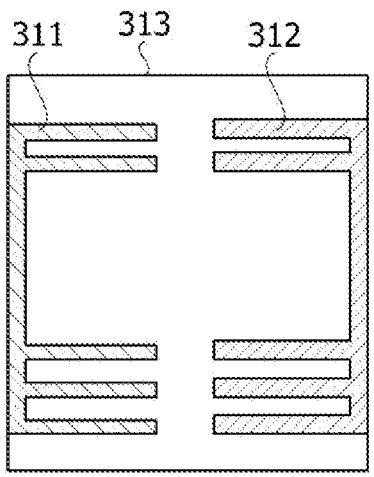
FIG. 14 is a view illustrating a variety of shapes of a sensing area of the pressure detecting insole according to yet another embodiment of the present invention.
Figure 14:
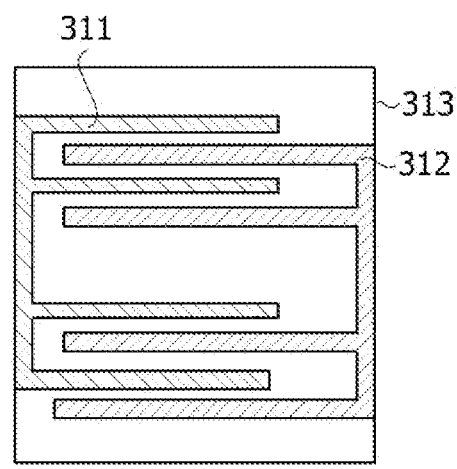
Figure 14:
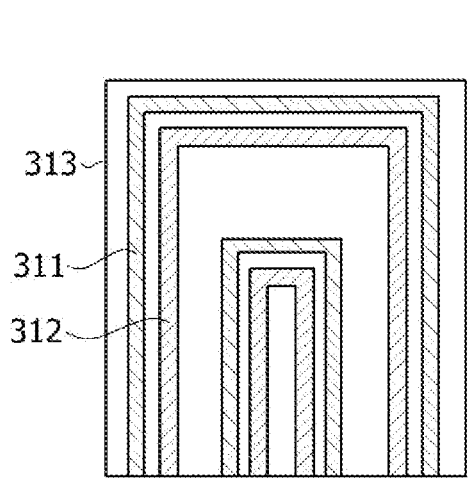
Figure 14:
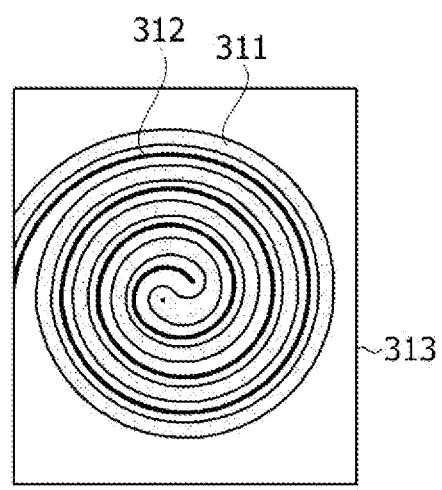

FIG. 14 is a view illustrating a variety of shapes of the sensing area of the pressure detecting insole according to yet another embodiment of the present invention.

Referring to FIG. 14, the first electrode 311 and the second electrode 312 may be arranged to be spaced apart from each other in a variety of shapes in the sensing area 313. As an example, the first electrode 311 and the second electrode 312 in the sensing area 313 may have a shape of teeth of a comb (refer to FIG. 14(*a*)).

Also, the first electrode 311 and the second electrode 312 having the shape of teeth of a comb may be arranged to face each other (refer to FIG. 14(*b*)). In addition, the first electrode 311 and the second electrode 312 having the shape of teeth of a comb may be arranged to overlap with each other (refer to FIG. 14(*c*)).

Also, the first electrode 311 and the second electrode 312 in the sensing area 313 may have a repetitively alternating spiral shape (refer to FIG. 14(*d*)). As described above, the first electrode 311 and the second electrode 312 may have a variety of shapes in the sensing area and the number of electrodes which overlap with each other in the sensing area 313 may be increased to increase an area which receives an electrical signal generated by a pressure so as to greatly increase sensor sensitivity.

Although the embodiments have been described above, the embodiments are merely an example and are not intended to limit the present invention. It should be understood by one of ordinary skill in the art that a variety of modifications and applications which are not exemplified above may be made without departing from the essential features of the present invention. For example, the components shown in detail in the embodiments may be modified. Also, differences related to the modifications and applications will be interpreted as being included in the scope of the present invention defined by the attached claims.

The invention claimed is:

1. A pressure detecting sensor comprising:
   an elastic layer comprising a hole; and
   an electrode layer comprising a plurality of electrodes which are arranged to be spaced apart on the elastic layer, the plurality of electrodes include a first electrode and a second electrode,
   wherein the elastic layer comprises a variable member disposed in the hole, the variable member having a first surface and a second surface, the first surface of the variable member facing the first electrode, a space is provided between the first electrode and the first surface of the variable member, and a thickness of the variable member is a distance between the first surface and the second surface,
   wherein the plurality of electrodes are electrically connected by an external pressure,
   wherein the first electrode covers a part of the hole,
   wherein the variable member comprises a conductive compound, and wherein based on pressure applied to a sensing area of the pressure sensing sensor, the thickness of the variable member between the first surface and the second surface is to decrease, and a resistance of the variable member is to change based on a change of the thickness of the variable member.

2. The pressure detecting sensor of claim 1, wherein the first surface of the variable member is disposed above a top surface of the elastic layer so as to form a step.

3. The pressure detecting sensor of claim 1, wherein an area in which the plurality of electrodes come into contact with a top surface of the elastic layer is smaller than an area of bottom surfaces of the plurality of electrodes.

4. The pressure detecting sensor of claim 1, wherein the plurality of electrodes comprise:
   the first electrode; and
   the second electrode which is disposed to be spaced apart from the first electrode and has a different polarity from that of the first electrode.

5. The pressure detecting sensor of claim 4, wherein the first electrode and the second electrode comprise conductive fibers, and
   wherein the conductive fibers are metal wires or fibers coated with metal films on surfaces thereof.

6. The pressure detecting sensor of claim 1, comprising an adhesive layer disposed in an area of the electrode layer except an area in which the hole is formed.

7. The pressure detecting sensor of claim 1, comprising an adhesive member disposed on the hole of the elastic member, and to surround the variable member within the hole.

8. The pressure detecting sensor of claim 1, wherein the elastic layer comprises a plurality of layers.

9. The pressure detecting sensor of claim 1, wherein the variable member connects the plurality of electrodes disposed to be spaced apart by the external pressure.

10. The pressure detecting sensor of claim 1, wherein the variable member comprises an elastic body, and
    wherein the elastic body comprises a conductive compound.

11. The pressure detecting sensor of claim 10, wherein the elastic body comprises one selected from the group consisting of a fiber material having a random arrangement such as foam, non-woven fabric, a nanoweb and the like, polyurethane, nylon, polyethylene terephthalate, and polyester.

12. The pressure detecting sensor of claim 10, wherein the conductive compound has 1 wt % to 10 wt % of the elastic body.

13. The pressure detecting sensor of claim 10, wherein the conductive compound comprises conductive polymers and conductive powder, and
    wherein a diameter of the conductive powder is 10 nm to 500 μm.

14. The pressure detecting sensor of claim 1, wherein the first surface of the variable member is disposed above a top surface of the elastic layer, and
    wherein the second surface of the variable member is disposed below a bottom surface of the elastic layer.

15. The pressure detecting sensor of claim 1, wherein the first surface of the variable member is disposed below a top surface of the elastic layer.

16. The pressure detecting sensor of claim 1, further comprising an adhesive layer disposed between the elastic layer and the first electrode.

17. The pressure detecting sensor of claim 16, wherein an area in which the plurality of electrodes come into contact with a top surface of the adhesive layer is smaller than an area of bottom surfaces of the plurality of electrodes.

18. The pressure detecting sensor of claim 1, wherein the first electrode is to face the second electrode.

19. The pressure detecting sensor of claim 18, wherein the elastic layer is disposed between the first electrode and the second electrode.

20. A pressure detecting insole comprising:
    a plurality of pressure detecting sensors; and
    a connector portion connected to the plurality of pressure detecting sensors,
    wherein each of the pressure detecting sensors comprises:
      an elastic layer comprising a hole; and
      an electrode layer comprising a plurality of electrodes arranged to be spaced apart on the elastic layer, the plurality of electrodes include a first electrode and a second electrode,
    wherein the elastic layer comprises a variable member disposed in the hole, the variable member having a first surface and a second surface, the first surface of the variable member facing the first electrode, a space is provided between the first electrode and the first surface of the variable member, and a thickness of the variable member is a distance between the first surface and the second surface,
    wherein the plurality of electrodes are electrically connected by an external pressure,
    wherein the first electrode covers a part of the hole, and
    wherein the variable member comprises a conductive compound, in response to pressure applied to the pressure sensing sensor, the thickness of the variable member between the first surface and the second surface is to decrease, and a resistance of the variable member is changed due to the change in the thickness of the variable member.

* * * * *